(12) United States Patent
Ujvari

(10) Patent No.: US 9,651,355 B2
(45) Date of Patent: May 16, 2017

(54) PROXIMITY DETECTION

(71) Applicant: Atmel Corporation, San Jose, CA (US)

(72) Inventor: Daniel Arthur Ujvari, Hauppauge, NY (US)

(73) Assignee: Atmel Corporation, San Jose, CA (US)

(*) Notice: Subject to any disclaimer, the term of this patent is extended or adjusted under 35 U.S.C. 154(b) by 363 days.

(21) Appl. No.: 13/846,458

(22) Filed: Mar. 18, 2013

(65) Prior Publication Data

US 2014/0009171 A1 Jan. 9, 2014

Related U.S. Application Data

(63) Continuation of application No. 12/910,484, filed on Oct. 22, 2010, now Pat. No. 8,400,209.

(51) Int. Cl.
| | | |
|---|---|---|
| *G01R 27/04* | (2006.01) | |
| *G01R 27/32* | (2006.01) | |
| *G01B 7/14* | (2006.01) | |
| *G01R 27/00* | (2006.01) | |
| *G01R 27/26* | (2006.01) | |
| *G01N 22/00* | (2006.01) | |
| *H03K 17/955* | (2006.01) | |

(Continued)

(52) U.S. Cl.
CPC ............... *G01B 7/14* (2013.01); *G01N 22/00* (2013.01); *G01R 27/00* (2013.01); *G01R 27/04* (2013.01); *G01R 27/2605* (2013.01); *H03K 17/955* (2013.01); *G01R 23/00* (2013.01); *G01R 27/32* (2013.01); *H03K 2017/9606* (2013.01)

(58) Field of Classification Search
CPC .................. G01B 7/14; H03K 17/955; H03K 2017/9606; G01N 22/00; G01R 27/2605; G01R 27/00; G01R 27/04; G01R 27/32; G01R 23/00

USPC .......... 324/76.11–76.83, 600, 605, 629, 647, 324/665, 672, 679, 705
See application file for complete search history.

(56) References Cited

U.S. PATENT DOCUMENTS

| | | | | |
|---|---|---|---|---|
| 4,345,167 | A | * | 8/1982 | Calvin .......................... 327/517 |
| 5,315,884 | A | * | 5/1994 | Kronberg ................ G01L 3/106 324/671 |
| 6,081,185 | A | * | 6/2000 | Portet ...................... 340/426.36 |

(Continued)

FOREIGN PATENT DOCUMENTS

WO WO 2012/129247 9/2012

OTHER PUBLICATIONS

U.S. Appl. No. 61/454,936, filed Mar. 21, 2011, Myers.
U.S. Appl. No. 61/454,950, filed Mar. 21, 2011, Lynch.
U.S. Appl. No. 61/454,894, filed Mar. 21, 2011, Rothkopf.

*Primary Examiner* — Huy Q Phan
*Assistant Examiner* — Raul Rios Russo
(74) *Attorney, Agent, or Firm* — Baker Botts L.L.P.

(57) ABSTRACT

In certain embodiments, a proximity sensor includes a sensing element, an oscillator connected to the sensing element, and control circuitry connected to the oscillator. The sensing element has a capacitance to ground that is variable as a function of the proximity of an object to the sensing element. The oscillator includes a capacitor. The control circuitry is configured to supply an excitation to the oscillator and a charge to the sensing element, and to measure the resonant frequency of the oscillator. The control circuitry provides a signal indicative of the proximity of the object to the sensing element.

20 Claims, 4 Drawing Sheets

(51) Int. Cl.
*G01R 23/00* (2006.01)
*H03K 17/96* (2006.01)

(56) References Cited

U.S. PATENT DOCUMENTS

| | | | |
|---|---|---|---|
| 6,466,036 B1 | 10/2002 | Philipp | |
| 6,911,829 B2 * | 6/2005 | Hilliard | G08G 1/042 324/546 |
| 7,663,607 B2 | 2/2010 | Hotelling et al. | |
| 7,864,503 B2 | 1/2011 | Chang | |
| 7,875,814 B2 | 1/2011 | Chen | |
| 7,920,129 B2 | 4/2011 | Hotelling et al. | |
| 8,031,094 B2 | 10/2011 | Hotelling et al. | |
| 8,031,174 B2 | 10/2011 | Hamblin et al. | |
| 8,040,326 B2 | 10/2011 | Hotelling | |
| 8,049,732 B2 | 11/2011 | Hotelling et al. | |
| 8,179,381 B2 | 5/2012 | Frey | |
| 8,217,902 B2 | 7/2012 | Chang | |
| 2002/0149376 A1 * | 10/2002 | Haffner | G01V 3/101 324/635 |
| 2002/0167439 A1 * | 11/2002 | Bloch | G01D 5/2013 342/28 |
| 2003/0071639 A1 * | 4/2003 | Haag | H03K 17/955 324/674 |
| 2005/0093638 A1 * | 5/2005 | Lin | H03L 1/026 331/176 |
| 2005/0277198 A1 * | 12/2005 | Shortes | G01N 29/036 436/149 |
| 2006/0071734 A1 * | 4/2006 | McCorquodale | H03B 5/06 331/176 |
| 2007/0089513 A1 * | 4/2007 | Rosenau | G01D 5/24 73/514.32 |
| 2008/0297175 A1 | 12/2008 | Wu | |
| 2008/0309635 A1 | 12/2008 | Matsuo | |
| 2009/0219039 A1 * | 9/2009 | Fasshauer | 324/682 |
| 2009/0315854 A1 | 12/2009 | Matsuo | |
| 2010/0148799 A1 * | 6/2010 | Hardie | 324/654 |
| 2010/0156629 A1 * | 6/2010 | Sexton | G01D 21/00 340/540 |
| 2011/0308320 A1 * | 12/2011 | Rocznik | G01L 9/125 73/702 |
| 2012/0242588 A1 | 9/2012 | Myers | |
| 2012/0242592 A1 | 9/2012 | Rothkopf | |
| 2012/0243151 A1 | 9/2012 | Lynch | |
| 2012/0243719 A1 | 9/2012 | Franklin | |
| 2013/0076612 A1 | 3/2013 | Myers | |

* cited by examiner

| # | S1 | S2 | S3 | NOTES |
|---|---|---|---|---|
| 1 | CLOSED | OPEN | CLOSED | Cx and Cs discharge |
| 2 | OPEN | OPEN | OPEN | Float Cs |
| 3 | OPEN | CLOSED | OPEN | Charge transfer |
| 4 | OPEN | OPEN | OPEN | Float Cs and settling time |
| 5 | CLOSED | OPEN | OPEN | Discharge Cx and Compare Vcs | repeat

PROXIMITY DETECTION

RELATED APPLICATION

This nonprovisional application is a divisional of U.S. application Ser. No. 12/910,484, filed Oct. 22, 2010 and entitled "Proximity Detection."

BACKGROUND

A proximity sensor detects the presence of a nearby person or object in a region or area. A proximity sensor may employ an electromagnetic or electrostatic field, or a beam of electromagnetic radiation, e.g., infrared, or acoustic energy and detect changes in the field or return signal. Proximity sensing can utilize different sensor types for different types of target objects. For example a photoelectric sensor might be suitable for a plastic target; an inductive proximity sensor might be used to detect a metal target.

Different types of proximity sensors have different maximum distances within which the sensors can detect an object. Some sensors have adjustments of the nominal distance range or means to report a graduated detection distance. Proximity sensors can have a high reliability and long functional life because of the absence of mechanical parts and lack of physical contact between sensor and the sensed object.

SUMMARY

The following disclosure describes examples of proximity detection and proximity sensors. Capacitance of a sensing element to ground is measured as an object moves into or out of proximity to the sensing element.

In certain embodiments, a proximity sensor includes a sensing element, an oscillator connected to the sensing element, and control circuitry connected to the oscillator. The sensing element has a capacitance to ground that is variable as a function of the proximity of an object to the sensing element. The oscillator includes a capacitor. The control circuitry is configured to supply an excitation to the oscillator and a charge to the sensing element, and to measure the resonant frequency of the oscillator. The control circuitry provides a signal indicative of the proximity of the object to the sensing element.

BRIEF DESCRIPTION OF THE DRAWINGS

The drawing figures depict one or more implementations in accordance with the present teachings, by way of example only, not by way of limitation. In the figures, like reference numerals refer to the same or similar elements.

DETAILED DESCRIPTION

In the following detailed description, numerous specific details are set forth by way of examples in order to illustrate the relevant teachings. In order to avoid unnecessarily obscuring aspects of the present teachings, those methods, procedures, components, and/or circuitry that are well-known to one of ordinary skill in the art have been described at a relatively high-level.

The examples shown and described implement a form of proximity detection utilizing detection of capacitance of a sensing element, relative to ground, as objects move into or out of proximity to the sensing element. For example, the proximity detection may occur over significant distances from a proximity sensor, compared to the dimensions of the sensor, or when the proximity sensor is touched by a person or other target object.

Reference now is made in detail to the examples illustrated in the accompanying figures and discussed below.

Figures 1, 2:
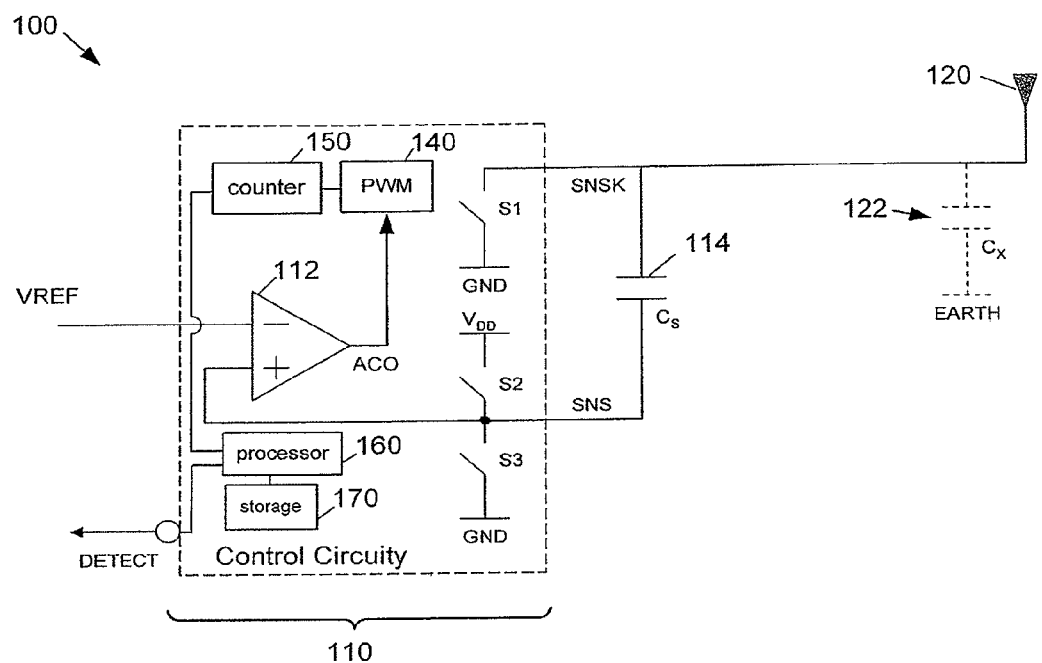
FIG. 1 is a circuit diagram of an example of a proximity sensor utilizing capacitive charge transfer.
FIG. 2 illustrates a switching table depicting a switching sequence of the three switches of the sensor circuit of FIG. 1.

The circuit diagram of FIG. 1 illustrates schematically the circuit of an example of a proximity sensor 100 that utilizes capacitive charge transfer for proximity detection. Sensor 100 may include control circuitry 110, a sample capacitor 114, and a sensing element, e.g., an antenna 120. Sensor 100 senses changes in capacitance of the antenna 120 to ground $C_x$, as indicated by capacitance 122. Sample capacitor 114 may be selected to be much larger than anticipated values of $C_x$. The control circuitry 110 may include switching functionality to charge the sample capacitor 114 and the capacitance to be measured $C_x$. The control circuitry 110 may also include switching functionality to selectively discharge the sample capacitor 114 and/or antenna 120 and to allow for measurement of the voltage $V_{cs}$ across the sample capacitor 114. An example of how the switching functionality of control circuitry 110 may operate is described in further detail with regard to FIG. 2.

As a person or other object approaches or moves away from the antenna 120, changes in the capacitance $C_x$ of the antenna 120 will occur. For example, as a person approaches antenna 120, $C_x$ will increase, and as the person moves away from the antenna 120, $C_x$ will decrease. The change in $C_x$ produces a measurable effect, which can be utilized by the sensor 100 for proximity detection.

In the circuit depicted in FIG. 1, a first switching element S1 can be used to discharge sample capacitor $C_s$ and the capacitance to be measured $C_x$. The circuit can include a second switching element S2 and a third switching element S3 as shown. Any suitable switching elements can be used for switching elements S1-S3. For example, suitable transistors or relays can be used. The second switching element S2 can operate to selectively connect the circuit to a voltage source, e.g., $V_{dd}$. The voltage source $V_{dd}$ may supply a suitable voltage including, but not limited to, any voltage within a range of about 1.8 to about 5.5 V. When the second switching element S2 is closed, charge can be applied to the sample capacitor 114 and $C_x$ of the antenna 120. The third switching element S3 can operate to selectively connect the circuit to ground. An analog comparator 112 can be included to compare voltage on the $C_s$ capacitor to a reference voltage signal, indicated by VREF. Any suitable reference voltage may be used. The output of the comparator 112, e.g., analog comparator output ACO, can be used to determine when the voltage on $C_s$ has reached the reference voltage VREF. As $C_s$ and $C_x$ are in parallel, they form a capacitive voltage divider. The voltage on $C_s$ is consequently influenced by $C_x$. The lower the reference voltage, the more energy can be maintained in the antenna 120.

For measuring capacitance on $C_s$ as affected by $C_x$, the output of the comparator 112 can be provided to a clock input of a pulse width modulator (PWM) circuit 140. The PWM circuit 140 can be used to gate a counter 150 that is clocked at a suitable frequency to count the number of pulses during a specified time. The control circuitry 110 may also include a processor 160 and storage functionality 170, e.g., suitable ROM and/or RAM, for holding software instructions and buffered data. The processor 160 can receive the counter output and correlate the counter output to $C_s$, $C_x$, and the proximity of a person or object to the sensor 100. The output of the counter 150 as received by the processor 160 may be suitably filtered for reducing noise effects. The processor 160 can process the output of the counter 150 for detecting proximity of an object relative to the antenna 120. The control circuitry 110 can provide an output signal, e.g., as shown by the DETECT signal of FIG. 1, that is indicative of the presence or absence of a person or object within proximity of the sensor 100. The output signal of the control circuitry 110 may be a bit, a byte, or an analog signal if a D/A converter (not shown) is utilized. The output signal of the control circuitry 110 may indicate the presence or absence of one or more objects within proximity to the sensor 100 or may indicate a degree of proximity to the sensor. The control circuitry output signal may be used to indicate the presence or absence of an object within a detection range of the sensor 100. For example, the output signal may be used to produce an audible signal such as a particular tone or an optical signal such as a particular color when an object is detected. The sound or color may be changed to indicate a change in the proximity of an object to the sensor 100.

For some applications, a dynamic reference voltage may be used to alter the sensing functionality of sensor 100. Raising the reference voltage may lower the nominal range of the sensor, for example from one foot (30 cm) maximum sensing distance from the antenna down to a few millimeters maximum sensing distance for proximity detection of a touch. For example, a sensor such as sensor 100 may be placed in a child's toy bear. If a child were to approach within a specified distance, e.g., six inches or so, the bear could respond with a verbal response such as "pick me up," encouraging the child to hold the toy. The proximity detection of the sensor may then be changed, by simply altering the reference voltage of the sensor, to close proximity-based touch sensing, allowing the bear to subsequently respond to the child's actual touches. Dynamically changing the nominal detection range of a proximity sensor in such a way may add commercial value to the related good(s) or components.

The control circuitry 110 can be implemented, for example, by a suitable microcontroller, a field programmable gate array (FPGA), or other standard logic devices. For example, an ATtiny48 microcontroller, as made commercially available by ATMEL Corporation, and/or a suitable timer/counter may be used for implementation of the control circuitry 110. In an example, the sample capacitor 114 may have a nominal capacitance of 4.7 nF and be 10 percent X7R ceramic.

FIG. 2 illustrates a switching table 200 depicting a switching sequence of the three switches of FIG. 1 during a charge transfer cycle for operation of the sensor 100. Referring to the table, at step 1, switching elements S1 and S3 are closed while switching element S2 is open, grounding both capacitors and thereby allowing $C_s$ and $C_x$ to discharge. Next, at step 2, all switching elements are open, which allows the voltage on $C_s$ and $C_x$ to float. Following at step 3, switching elements S1 and S3 are open while switching element S2 is closed, applying voltage $V_{dd}$ to both capacitors and thereby allowing charge to transfer to $C_s$ and $C_x$. At step 4, all three switching elements S1-S3 are open, which allows voltage on $C_s$ and $C_x$ to float and settle. Following, at step 5, switching element 1 is closed while switching elements S2-S3 are open, allowing the charge in $C_x$ to discharge and for a comparison of the voltage on $C_s$ with the reference voltage, e.g., VREF in FIG. 1. The switching sequence of steps 2 to 5 may be repeated for later measurements of the capacitance. A desired number of repeated measurements using steps 2 to 5 can be performed. Changes in capacitance $C_x$ can be interpreted to detect movement of an object toward or away from the antenna 120.

Figure 3:
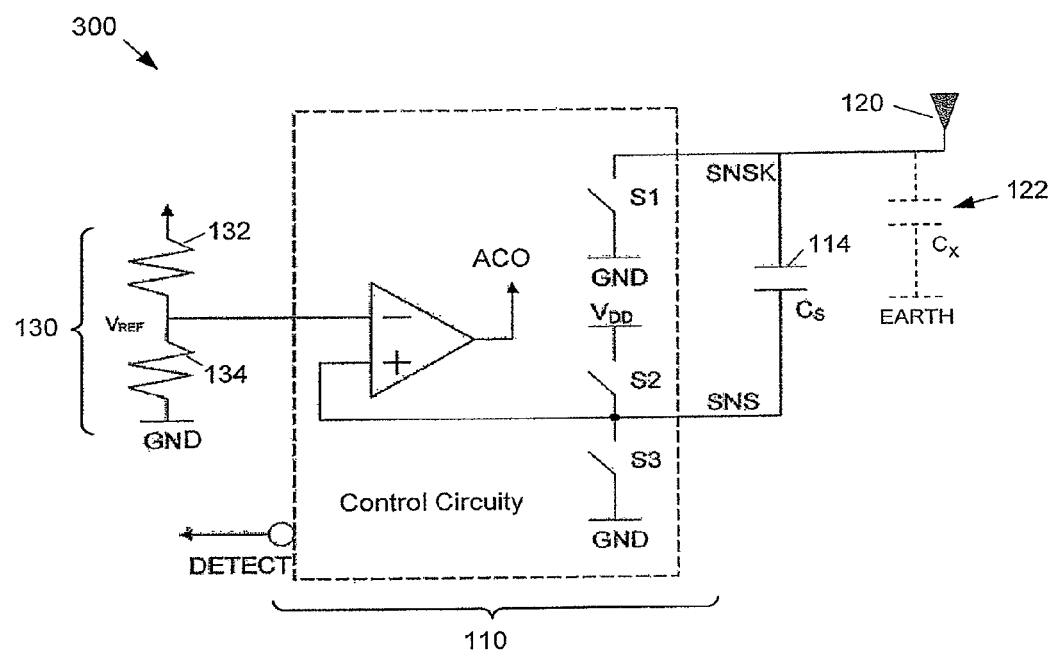
FIG. 3 illustrates a variation to the circuit of FIG. 1.

FIG. 3 illustrates schematically a variation 300 to the circuit of FIG. 1 with a reference voltage set by a voltage divider 130 including resistors 132 and 134 in series. Any desired values may be selected for resistors 132. and 134 so as to produce a desired reference voltage. The PWM, counter, processor, and storage are omitted to simplify the drawing.

Figure 4:
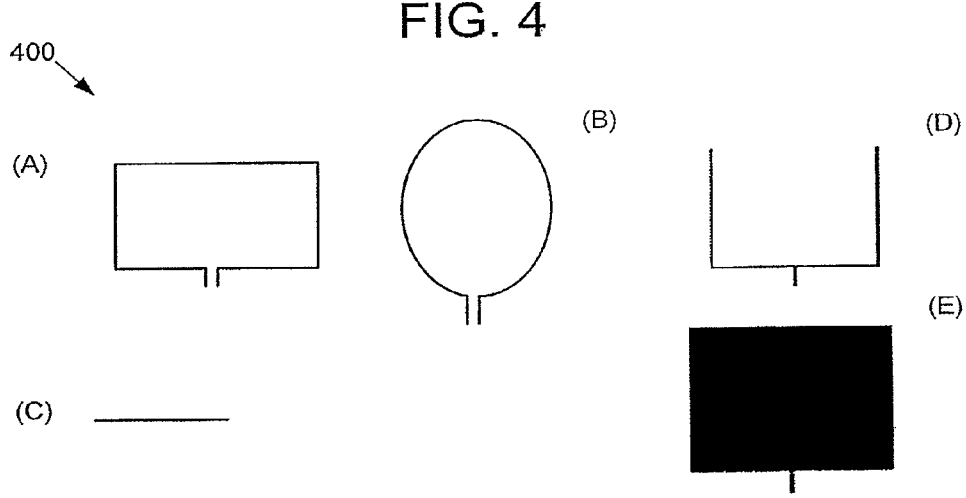
FIG. 4 illustrates schematically various antenna examples.

FIG. 4 illustrates schematically a collection 400 of antenna examples that may be used in a proximity sensor. Depicted in the drawing are a square loop antenna (A), a curved loop antenna (B), a line antenna (C), a dipole antenna (D), and a patch antenna (E). The configurations shown are representative, and other antenna configurations may be used for proximity detection.

For some proximity sensor applications, antennas may be configured for proximity detection in one general direction. In other applications, antennas may be configured for proximity detection in multiple directions. For antennas suitable for exemplary proximity sensors, plane charges such as produced by rectangular plates, e.g., as shown by the patch antenna (E), may offer good distance characteristics because the greatest field strength is expressed perpendicular to the surface of the plane. Such configurations, however, may allow limited space for related components of a proximity sensor or a device incorporating such a sensor, e.g., control circuitry, key pads, etc.

For some applications, electric field lines from a sensor antenna can be oriented to form a directional antenna and still offer available space within or adjacent to the antenna, e.g., within the perimeter of the antenna. In some applications, a square loop or dipole antenna may be used. Examples are shown in FIGS. 4 as (A), (B), and (D). For example, a proximity sensor using a rectangular loop or dipole antenna placed in the perimeter of a wall mounted device, e.g., a wall mounted thermostat or security keypad, may offer good proximity detection for approaches from all four sides. A sensor with such an antenna may also offer good detection distance when approached head on. Such head on proximity detection may be at distances greater than or equal to the dimensions of a particular antenna. For example, a 6-inch diameter curved loop antenna may provide reliable proximity detection at 12 inches from the plane of the antenna. Such a sensor using the curved loop antenna could also, or alternatively, be set so that one would have to actually touch the sensor housing/casing before being detected by the sensor.

Sensors or antennas configured as points, spheres and lines, because of their radial field spreading with distance, may be well suited for proximity detection in applications where the direction of approach is unknown or variable. As described previously, some applications may, however, require proximity detection from one general direction.

Figure 5:
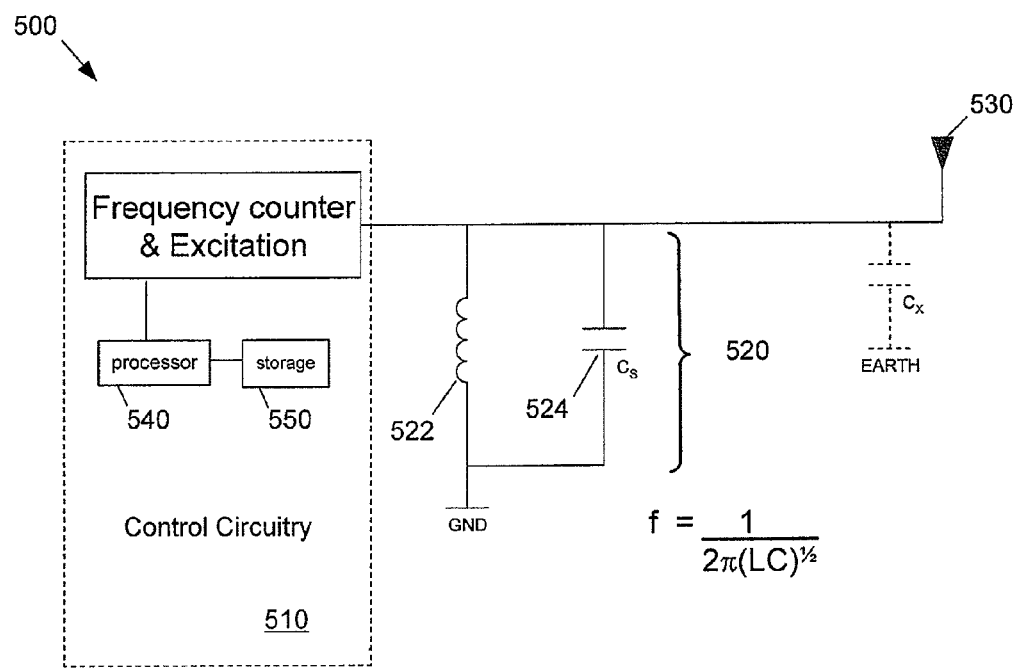
FIG. 5 is a circuit diagram of another example of a proximity sensor, utilizing a LC oscillator.

The exemplary proximity sensors can utilize other types of measurement of an antenna's capacitance to ground for proximity detection. FIG. 5 shows one such example in which the variable $C_x$ of an antenna is utilized to alter the resonant frequency of an LC circuit.

The circuit diagram of FIG. 5 illustrates schematically a proximity sensor 500 utilizing a LC oscillator. Proximity sensor 500 includes control circuitry 510, a tank circuit or LC oscillator 520, and a sensing element, e.g., antenna 530. The control circuitry 510 can include a suitable processor 540 and storage 550. The LC oscillator 520 includes inductor 522 and sample capacitor 524. The control circuitry 510 can include frequency counter and excitation functionality and can supply an excitation signal to the LC oscillator 520. The control circuitry 510 can also supply a charge to the antenna 530, which has a capacitance to free space or ground, $C_x$. The capacitance $C_x$ can be influenced by people or objects coming into and moving out of proximity to the sensor antenna 530. A microcontroller such as an Atmel® ATtiny48 microcontroller and/or a suitable timer/counter may be used for implementation of the control circuitry 510.

For sensor 500, as an object or person approaches or comes into proximity with the sensing element S30, the capacitance $C_x$ increases. As an object or person moves away and out of proximity to the sensing element S30, the capacitance $C_x$ decreases. Because $C_x$ is in parallel with $C_s$, the new $C_x$ changes the capacitance of the oscillator 520, changing the resonant frequency, f, where f is given by:

$$f = \frac{1}{2\pi\sqrt{LC}}$$

The control circuitry 510 can measure the change in the resonant frequency f, which can be correlated to capacitance $C_x$ and corresponding proximity of an object or person within range of the sensor 500.

In addition to proximity sensors utilizing oscillators according to FIG. 5, other types of resonant circuits and structures may be used in conjunction with a variable capacitance of a sensing element.

Figure 6:
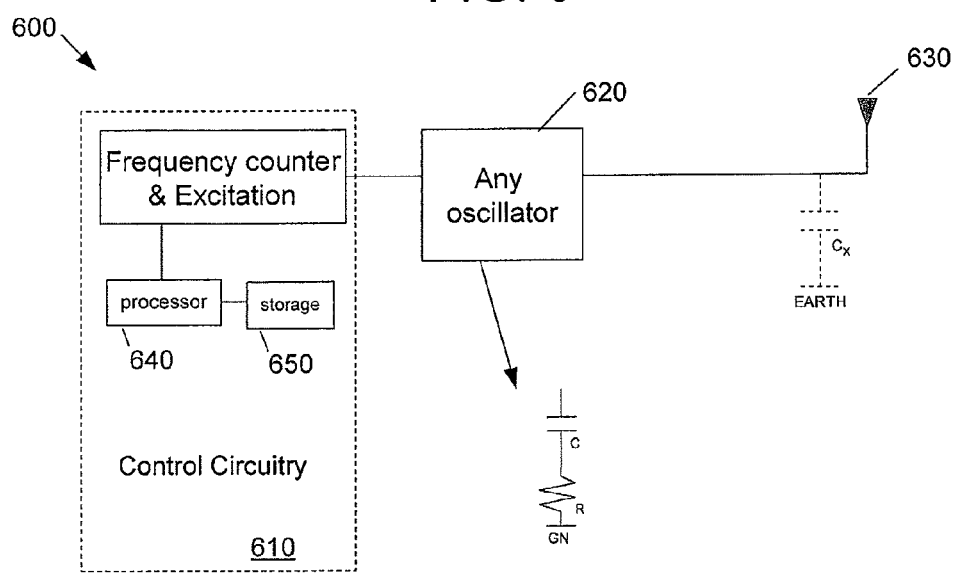
FIG. 6 is a circuit diagram of another example of a proximity sensor, utilizing a generic oscillator.

The circuit diagram of FIG. 6 illustrates schematically another example of a proximity sensor 600 utilizing a generic oscillator. Proximity sensor 600 includes control circuitry 610 and a generic oscillator 620 connected to a sensing element configured as an antenna 630. The control circuitry 610 can include a suitable processor 640 and storage 650. The control circuitry 610 can include frequency counter and excitation functionality. In exemplary embodiments, a microcontroller such as an Atmel® ATtiny48 microcontroller and/or a suitable timer/counter may be used for implementation of the control circuitry 610.

As indicated in FIG. 6, any electric oscillator affected by a change in capacitance $C_x$ may be used for proximity detection by sensor 600. Examples may include, but are not limited to, RC network oscillators such as a Wien bridge oscillator, a twin T oscillator, and the like, or RLC networks. Changes in $C_x$ will change the resonant frequency of the oscillator 620. By recognizing the change in $C_x$, sensor 600 can provide for proximity detection. The detection range of the sensor 600 may be dynamically varied by adjusting the values of R and/or C in the oscillator 620, e.g., by switching in or out resistive or capacitive elements.

Figure 7:
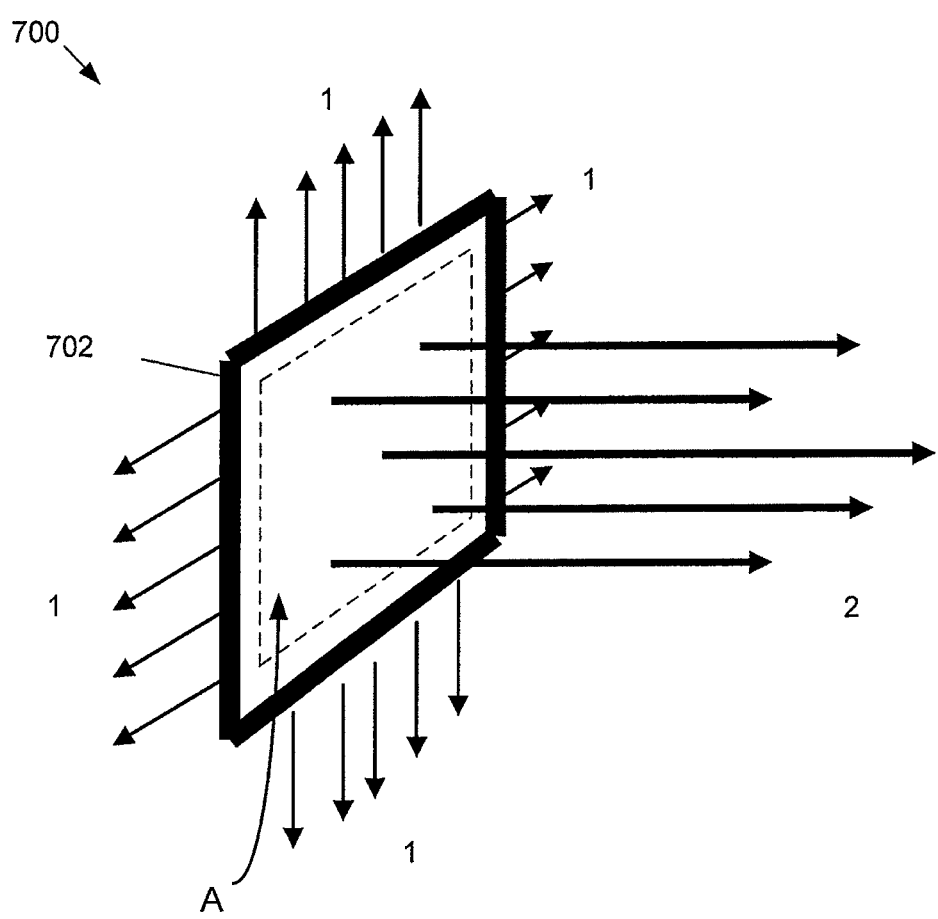
FIG. 7 illustrates schematically an example of an antenna configured as a loop antenna and shows field lines emanating from the antenna.

FIG. 7 illustrates schematically an antenna 700 configured as a loop antenna and shows field lines emanating from the antenna. Antenna 700 is configured as a rectangular loop, shown with perimeter 702. Because of the field features, rectangular loop antennas can provide both lateral proximity detection and proximity detection in orthogonal directions. In FIG. 7, electric field lines for lateral proximity detection are indicated by field lines 1, and electric field lines for orthogonal or head on directions are indicated by field lines 2.

With continued reference to FIG. 7, the open area A within the perimeter of the antenna 700 may be utilized for components that are to be used in conjunction with the proximity sensor. For example, the area within the dashed lines within perimeter 702 may be used for a keypad or card reader or other components of a device that incorporates a proximity sensor that includes the antenna 700.

Some implementations of proximity detection may involve programming. For example, a microcontroller may include firmware facilitating the control of the switching functionality for charging and discharging a sample capacitor and antenna of a proximity sensor as shown in the table of FIG. 2 and the measuring of capacitance to detect proximity. An article of manufacture may include the program, e.g., executable code and/or associated data, carried on or embodied in a machine readable medium. A machine readable medium may take many forms, including but not limited to, a tangible non-transitory storage medium, a carrier wave medium, or physical transmission medium. Non-volatile types of non-transitory, tangible storage media include any or all of the memory of the supporting electronics of a proximity sensor, computing devices, processors or the like, or associated modules thereof, such as various semiconductor memories, tape drives, disk drives and the like, which may provide storage at any time for the programming. All or portions of the programming may at times be communicated through the Internet or various other telecommunication networks. Such communications, for example, may enable loading of the programming from one computer or processor into another computer or processor, e.g., for installation in a microcontroller. Thus, another type of media that may bear the programming includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software.

Various modifications may be made to the examples and embodiments described in the foregoing description, and any related teachings may be applied in numerous applications, only some of which have been described herein. It is intended by the following claims to claim any and all applications, modifications and variations that fall within the true scope of the present teachings.

What is claimed is:

1. A proximity sensor comprising:
   a sensing element having a capacitance to ground that is variable as a function of a proximity of an object to the sensing element;
   an oscillator connected to the sensing element, wherein the oscillator includes a capacitor; and
   control circuitry connected to the oscillator, the control circuitry configured to:
   supply an excitation to the oscillator and a charge to the sensing element;
   measure a resonant frequency of the oscillator, wherein the capacitance of the sensing element is in parallel with the capacitor of the oscillator such that changes to the capacitance of the sensing element change a capacitance of the oscillator, changing the resonant frequency of the oscillator; and provide a signal indicative of the proximity of the object to the sensing element.

2. The proximity sensor of claim 1, wherein the oscillator comprises a LC tank circuit.

3. The proximity sensor of claim 1, wherein the oscillator comprises a RC network.

4. The proximity sensor of claim 1, wherein the sensing element comprises an antenna.

5. The proximity sensor of claim 1, wherein the control circuitry is further configured to dynamically vary a detection range of the proximity sensor.

6. The proximity sensor of claim 4, wherein the antenna comprises a loop antenna.

7. The proximity sensor of claim 1, wherein the oscillator comprises a twin T oscillator.

8. The proximity sensor of claim 1, wherein the oscillator comprises an RLC network.

9. The proximity sensor of claim 1, wherein:
the oscillator comprises an LC circuit; and
the resonant frequency of the oscillator is given by the following:

$$f = \frac{1}{2\pi\sqrt{LC}}.$$

10. The proximity sensor of claim 5, wherein:
the oscillator comprises a RC network; and
wherein the control circuitry is configured to dynamically vary the detection range of the proximity sensor by adjusting values of one or more of resistance and capacitance in the oscillator.

11. A proximity sensor controller, comprising:
control circuitry adapted to be connected to an oscillator and a sensing element, the sensing element having a capacitance to ground that is variable as a function of proximity of an object to the sensing element, the control circuitry configured to execute instructions that cause the control circuitry to perform operations to measure a change in a resonant frequency of the oscillator, the operations comprising:
supplying an excitation signal to the oscillator, the oscillator comprising a capacitor;
supplying a charge to the sensing element;
measuring the change in the resonant frequency of the oscillator, wherein the capacitance of the sensing element is in parallel with the capacitor of the oscillator such that changes to the capacitance of the sensing element change a capacitance of the oscillator, changing the resonant frequency of the oscillator; and
providing a signal indicative of the proximity of the object to the sensing element.

12. The proximity sensor controller of claim 11, wherein the oscillator comprises a LC tank circuit.

13. The proximity sensor controller of claim 11, wherein the oscillator comprises a RC network.

14. The proximity sensor controller of claim 11, wherein the sensing element comprises an antenna.

15. The proximity sensor controller of claim 11, wherein the control circuitry is further configured to perform operations comprising dynamically varying a detection range of a proximity sensor with which the proximity sensor controller operates.

16. An article of manufacture comprising:
a non-transitory machine readable storage medium; and
executable program instructions embodied in the non-transitory machine readable storage medium that when executed by a processor of a programmable computing device configures the programmable computing device to control a proximity sensor having control circuitry connected to an oscillator and a sensing element, wherein the sensing element has a capacitance to ground that is variable as a function of the proximity of a person or object to the sensing element, to perform operations to measure the change in the resonant frequency of the oscillator, including operations to:
supply an excitation signal to the oscillator;
supply a charge to the sensing element;
measure the change in the resonant frequency of the oscillator, wherein the capacitance of the sensing element is in parallel with the capacitor of the oscillator such that changes to the capacitance of the sensing element change a capacitance of the oscillator, changing the resonant frequency of the oscillator; and
provide a signal indicative of the proximity of the object to the sensing element.

17. The article of manufacture of claim 16, wherein the oscillator comprises a LC tank circuit.

18. The article of manufacture of claim 16, wherein the oscillator comprises a RC network.

19. The article of manufacture of claim 16, wherein the sensing element comprises an antenna.

20. The article of manufacture of claim 16, wherein the control circuitry is further configured to dynamically vary the detection range of the proximity sensor.

* * * * *

UNITED STATES PATENT AND TRADEMARK OFFICE
CERTIFICATE OF CORRECTION

PATENT NO. : 9,651,355 B2  
APPLICATION NO. : 13/846458  
DATED : May 16, 2017  
INVENTOR(S) : Daniel Arthur Ujvari et al.

Page 1 of 1

It is certified that error appears in the above-identified patent and that said Letters Patent is hereby corrected as shown below:

On the Title Page

Under (63): Before "of application No. 12/910,484, filed on" delete "Continuation" and insert --Divisional--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*